United States Patent
Alotaibi et al.

(10) Patent No.: US 9,427,292 B1
(45) Date of Patent: Aug. 30, 2016

(54) ADJUSTABLE FIXATOR FOR SCANNING DENTAL CASTS

(71) Applicant: KING SAUD UNIVERSITY, Riyadh (SA)

(72) Inventors: Hanan Nejer Sahil Alotaibi, Riyadh (SA); Waled Mohammed Alshhrani, Vancouver (CA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/965,812

(22) Filed: Dec. 10, 2015

(51) Int. Cl.
*A61C 11/00* (2006.01)
*A61C 11/08* (2006.01)

(52) U.S. Cl.
CPC ............ *A61C 11/003* (2013.01); *A61C 11/001* (2013.01); *A61C 11/087* (2013.01)

(58) Field of Classification Search
CPC ......... B25B 5/00; B25B 5/067; B25B 5/068; B25B 5/082
See application file for complete search history.

(56) References Cited

U.S. PATENT DOCUMENTS

| | | | | |
|---|---|---|---|---|
| 1,587,820 A | * | 6/1926 | Carter | ...................... B25B 5/101 269/140 |
| 3,150,448 A | | 9/1964 | Wozar | |
| 3,841,609 A | * | 10/1974 | Smith | .................. E04G 21/3233 248/231.61 |
| 3,863,900 A | * | 2/1975 | Dagiel | ................ E04G 21/3233 248/231.71 |
| 5,064,368 A | | 11/1991 | Lavin | |
| 5,219,282 A | | 6/1993 | Lavin | |
| 5,349,979 A | * | 9/1994 | Zeien | ...................... B25B 5/068 137/318 |
| 6,971,641 B1 | * | 12/2005 | Sherwin | .................. B25B 5/068 269/166 |
| 2006/0177794 A1 | | 8/2006 | Yau et al. | |
| 2008/0131838 A1 | | 6/2008 | Matsuda et al. | |
| 2008/0166679 A1 | | 7/2008 | Huffman | |
| 2008/0259411 A1 | | 10/2008 | Karlsson | |
| 2010/0240001 A1 | | 9/2010 | Steger | |

FOREIGN PATENT DOCUMENTS

FR          2 446 629          8/1980

* cited by examiner

*Primary Examiner* — Lee D Wilson
(74) *Attorney, Agent, or Firm* — Richard C. Litman

(57) ABSTRACT

The adjustable fixator for scanning dental casts includes upper and lower plates which are adapted for releasably securing a dental cast to be optically scanned therebetween. The upper and lower plates are selectively vertically adjustable with respect to one another, and a bottom surface of the lower plate is adapted for releasable mounting in an optical scanner. The upper plate is secured to a cylindrical shell which slidably receives a vertical support mounted to the lower plate, allowing the user to slidably adjust the height of the upper plate with respect to the lower plate. An engaging member mounted to the cylindrical support slides within a vertically extending slot formed through the cylindrical shell. The vertical position of the upper plate may be locked by sliding the engaging member into a selected one of a plurality of horizontally extending slots also formed through the cylindrical shell.

7 Claims, 4 Drawing Sheets

ADJUSTABLE FIXATOR FOR SCANNING DENTAL CASTS

BACKGROUND OF THE INVENTION

1. Field of the Invention

The present invention relates to the fabrication of dental prostheses, and more particularly to a vertically-adjustable fixator for holding dental casts during optical scanning thereof for preparation of a dental prosthesis.

2. Description of the Related Art

Three-dimensional (3D) optical scanners are commonly used in dentistry in order to create a 3D digital image of dental cast. Such 3D digital images can then be used with a milling machine or the like for fabrication of a dental prosthesis. An example of a commonly used 3D optical scanner used in dentistry is the Ceramill® Map400 scanner, manufactured by Amann Girrbach® GmbH of Germany. In order to properly position the dental cast within the optical scanning range of the scanner, the dental cast is typically supported by a transfer kit, such as exemplary transfer kit 100 of FIG. 2. As shown in FIG. 2, such a transfer kit 100 typically includes a fixator 112, which includes an upper plate 114 and a lower plate 116, both secured to, and separated by, a vertical support 118. The dental cast C is held therebetween for scanning. The lower plate 116 is secured to a fixation plate 120, which is adapted for mounting to the particular type of base plate used in the optical scanner. As shown, since the dental cast C must be held at a certain height within the optical scanning range of the scanner, one or more distance plates 122 may be connected to the fixation plate 120 for adjustably raising the height of the dental cast C with respect to the base plate in the scanner. The distance plates 122 are also adapted for secure mounting to the particular base plate used with the particular scanner.

Although such transfer kits are commonly available for use with a variety of optical scanners, assembling the various elements together for proper positioning of the dental cast can be very time consuming and also susceptible to human error, both in the assembly itself and in misjudging proper height and alignment of the dental cast with respect to the scanning range of the scanner. Thus, an adjustable fixator for scanning dental casts solving the aforementioned problems is desired.

SUMMARY OF THE INVENTION

The adjustable fixator for scanning dental casts includes upper and lower plates which are adapted for releasably securing a dental cast to be optically scanned therebetween. The upper and lower plates are selectively vertically adjustable with respect to one another, and a bottom surface of the lower plate is adapted for releasable mounting in an optical scanner. The upper plate has opposed front and rear ends and opposed top and bottom surfaces, and is sized and contoured for securing the dental cast or associated dental cast accessories (such as a conventional model holder, for example). Similarly, the lower plate also has opposed front and rear ends and opposed top and bottom surfaces, and is also sized and contoured for securing the dental cast or associated dental cast accessories (such as a conventional model holder).

A cylindrical support is mounted on the rear end of the lower plate and extends upwardly therefrom, and a corresponding cylindrical shell is mounted on the rear end of the upper plate and extends downwardly therefrom. The cylindrical support is slidably received within the cylindrical shell such that a height of the upper plate with respect to the lower plate is selectively adjustable. The cylindrical shell has a vertically extending slot and a plurality of horizontally extending slots formed therethrough, with the plurality of horizontally extending slots each being in open communication on one end thereof with the vertically extending slot.

An engaging member is mounted on the cylindrical support and extends radially therefrom, such that in a first angular position of the cylindrical shell with respect to the cylindrical support, the engaging member is slidable within the vertically extending slot, allowing the user to selectively adjust the height of the upper plate with respect to the lower plate. In a second angular position of the cylindrical shell with respect to the cylindrical support, the engaging member is received within a selected one of the plurality of horizontally extending slots to selectively and releasably lock the vertical position of the cylindrical shell with respect to the cylindrical support. The engaging member may be, for example, a threaded screw or the like, allowing the vertical position to be further releasably secured by engagement with a threaded nut or the like.

These and other features of the present invention will become readily apparent upon further review of the following specification.

BRIEF DESCRIPTION OF THE DRAWINGS

Unless otherwise indicated, similar reference characters denote corresponding features consistently throughout the attached drawings.

DETAILED DESCRIPTION OF THE PREFERRED EMBODIMENTS

Figure 1:
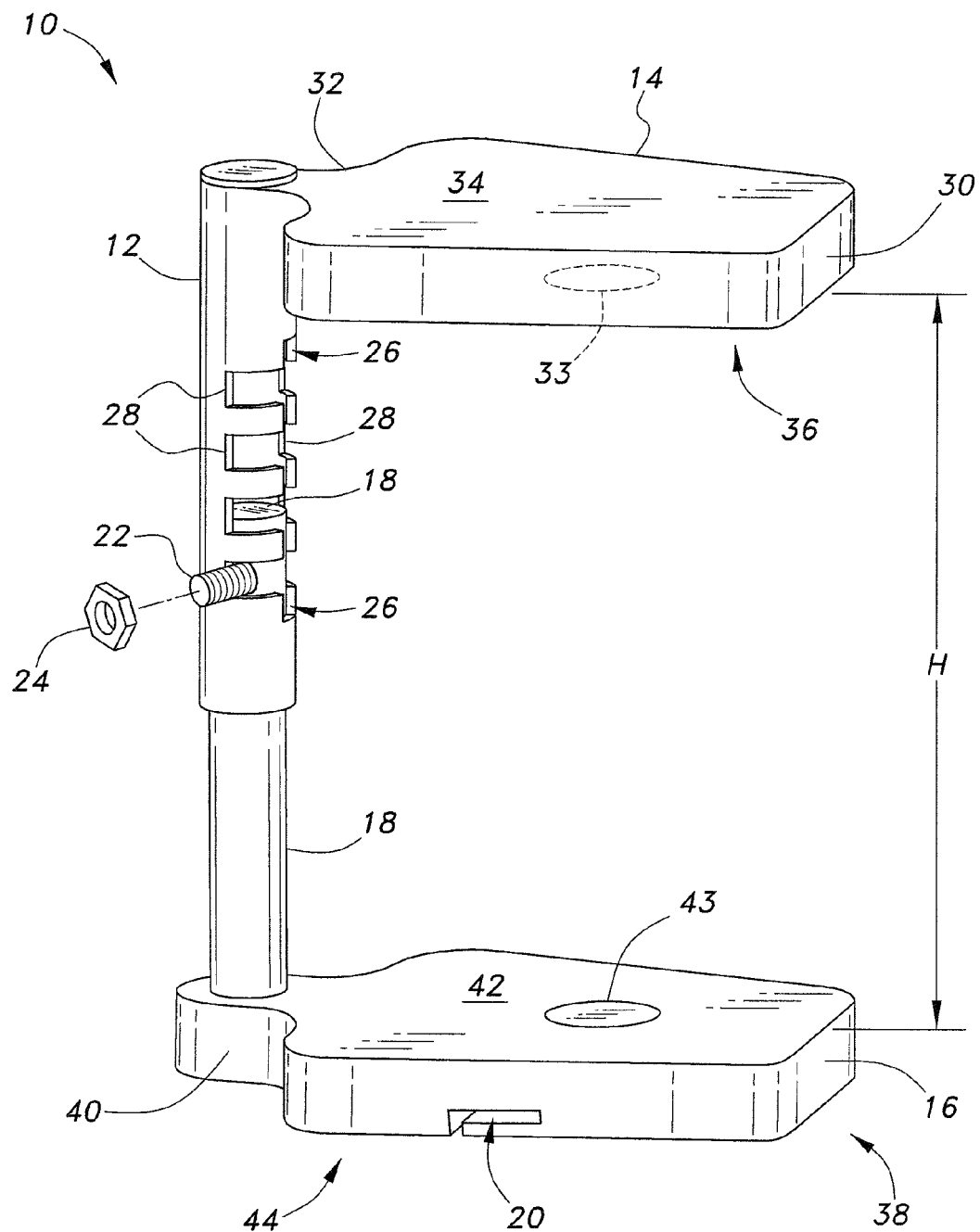
FIG. 1 is a perspective view of an adjustable fixator for scanning dental casts according to the present invention.
Figure 2:
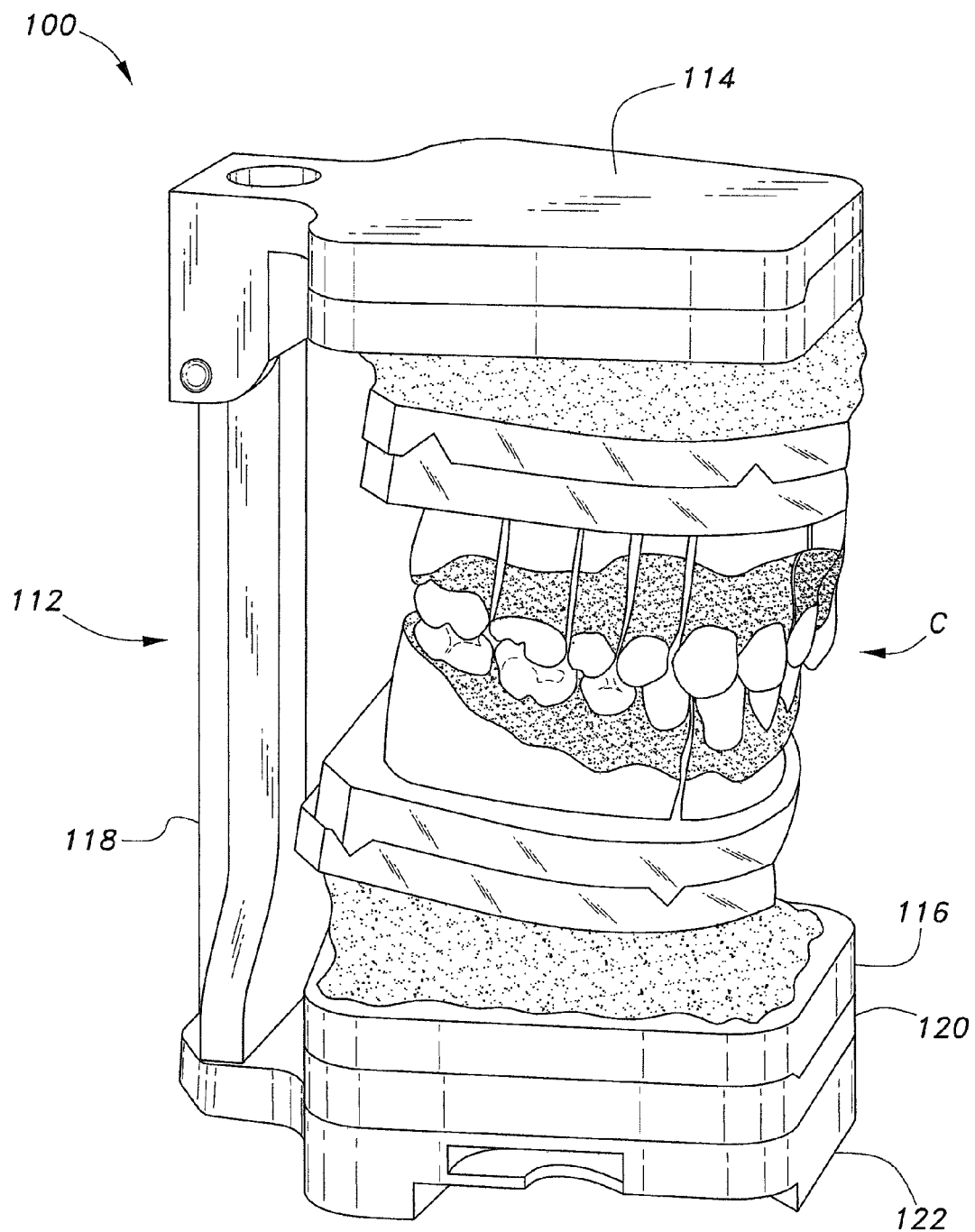
FIG. 2 is a perspective view of a prior art fixator for scanning dental casts.
Figure 3:
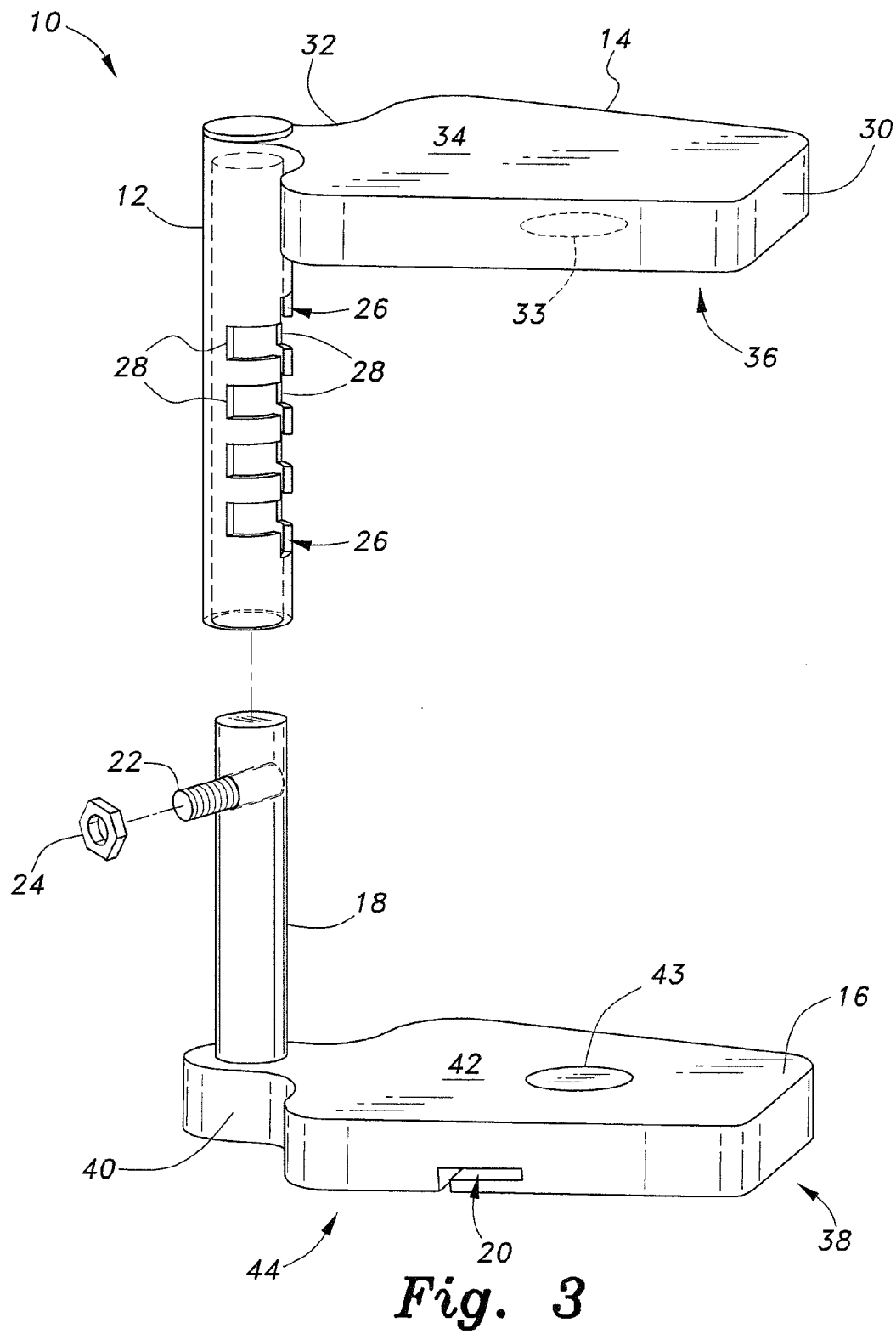
FIG. 3 is an exploded perspective view of the adjustable fixator for scanning dental casts according to the present invention.

As shown in FIGS. 1 and 3, the adjustable fixator for scanning dental casts 10 includes upper and lower plates 14, 16, respectively, which are adapted for releasably securing a dental cast or die to be optically scanned, such as exemplary dental cast C of FIG. 2, therebetween. The upper and lower plates 14, 16, respectively, are selectively vertically adjustable with respect to one another, and a bottom surface 44 of the lower plate 16 is adapted for releasable mounting in an optical scanner. The upper plate 14 has opposed front and rear ends 30, 32, respectively, and opposed top and bottom surfaces 34, 36, respectively, and is sized and contoured for securing the dental cast C or associated dental cast accessories (such as a conventional model holder, for example). The bottom surface 36 of the upper plate 14 includes a magnet 33. Similarly, the lower plate 16 has opposed front and rear ends 38, 40, respectively, and opposed top and bottom surfaces 42, 44, respectively, and is also sized and contoured for securing the dental cast C or associated dental cast accessories (such as a conventional model holder). The top surface 42 of the lower plate 16 includes a magnet 43.

It should be understood that the overall contouring, size and relative dimensions of upper plate 14 and lower plate 16 shown in FIGS. 1 and 3 are shown for exemplary purposes only.

A cylindrical support 18 is mounted on the rear end 40 of the lower plate 16 and extends upwardly therefrom, as shown. A corresponding cylindrical shell 12 is mounted on the rear end 32 of the upper plate 14 and extends downwardly therefrom. The cylindrical support 18 is slidably received within the cylindrical shell 12 such that height H of the upper plate 14 with respect to the lower plate 16 is selectively adjustable. Further, as shown, the cylindrical shell 12 has a vertically extending slot 26 and a plurality of horizontally extending slots 28 formed therethrough, with the plurality of horizontally extending slots 28 each being in open communication on one end thereof with the vertically extending slot 26. It should be understood that the length and width of the vertically extending slot 26 and each of the horizontally extending slots, as well as the number of horizontally extending slots 28, are shown for exemplary purposes only.

Figure 4A:
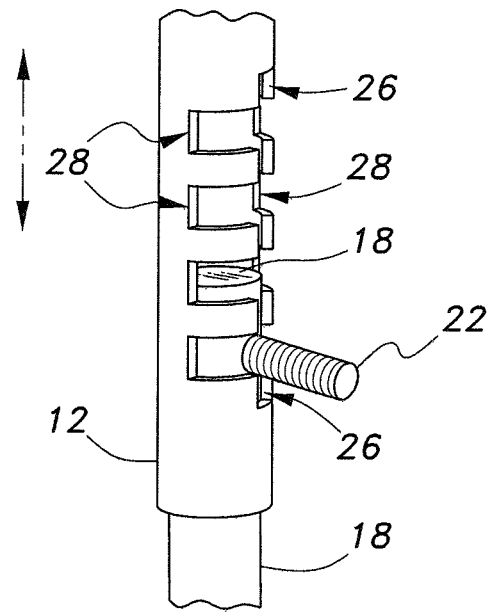
FIG. 4A is a partial perspective view showing selective vertical adjustment of a cylindrical shell of the adjustable fixator for scanning dental casts.
Figure 4B:
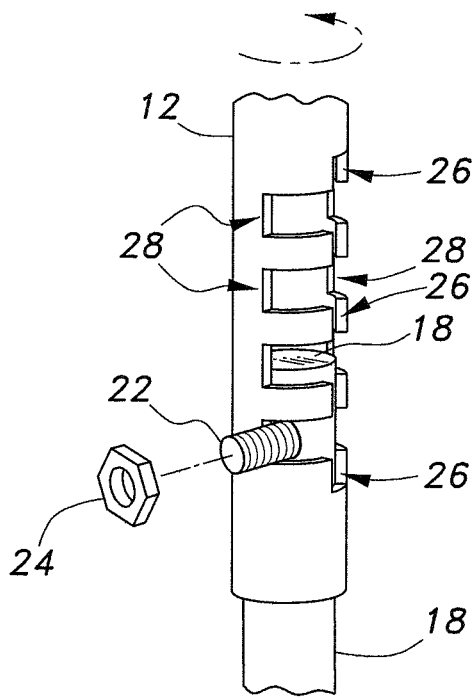
FIG. 4B is a partial perspective view showing locking of the cylindrical shell of FIG. 4A in a selected vertical position.

An engaging member 22 is mounted on the cylindrical support 18 and extends radially therefrom, such that in a first angular position of the cylindrical shell 12 with respect to the cylindrical support 18 (shown in FIG. 4A), the engaging member 22 is freely slidable within the vertically extending slot 26, allowing the user to selectively adjust the height of the upper plate 14 with respect to the lower plate 16. In a second angular position of the cylindrical shell 12 with respect to the cylindrical support 18 (shown in FIG. 4B), the engaging member 22 is received within a selected one of the plurality of horizontally extending slots 28 to selectively and releasably lock the vertical position of the cylindrical shell 12 with respect to the cylindrical support 18. The engaging member 22 may be, for example, a threaded screw or the like, allowing the vertical position to be further releasably secured by engagement with a threaded nut 24 or the like.

It should be understood that upper and lower plates 14, 16, cylindrical support 18 and cylindrical shell 12 may be formed from any suitable materials, such as metal, plastic or the like. Additionally, it should be understood that the adjustable fixator for scanning dental casts 10 may be used in combination with any suitable type of optical scanner or with any accessories specific to a particular optical scanner. For example, as shown in FIGS. 1 and 3, L-shaped recesses 20 are formed in the sides of lower plate 16. These are for receiving the particular type of clamp used with the base plate of the Ceramill® Map400 scanner, manufactured by Amann Girrbach® GmbH of Germany. However, it should be understood that additional features such as these, along with other securement devices, such as magnets or the like, as well as the overall contouring, size and relative dimensions of the various elements of the adjustable fixator for scanning dental casts 10, may be customized or varied for particular use with a specific type of scanner without departing from the spirit or scope of the present invention.

It is to be understood that the present invention is not limited to the embodiments described above, but encompasses any and all embodiments within the scope of the following claims.

We claim:

1. An adjustable fixator for scanning dental casts, comprising:
    an upper plate having opposed front and rear ends and having opposed top and bottom surfaces;
    a lower plate having opposed front and rear ends and having opposed top and bottom surfaces;
    a cylindrical support mounted on said lower plate and extending upwardly therefrom;
    a cylindrical shell mounted on said upper plate and extending downwardly therefrom, said cylindrical support being slidably received within said cylindrical shell such that a height of said upper plate with respect to said lower plate is selectively adjustable, said cylindrical shell having a vertically extending slot and a plurality of horizontally extending slots formed therethrough, the plurality of horizontally extending slots each being in open communication on one end thereof with the vertically extending slot; and
    an engaging member mounted on said cylindrical support and extending radially therefrom, wherein in a first angular position of said cylindrical shell with respect to said cylindrical support, said engaging member is slidable within the vertically extending slot, and in a second angular position between said cylindrical shell with respect to said cylindrical support, said engaging member is received within a selected one of the plurality of horizontally extending slots to selectively and releasably lock the vertical position of said cylindrical shell with respect to said cylindrical support,
    whereby said upper plate and said lower plate are adapted for releasably securing a dental cast to be scanned therebetween, the bottom surface of said lower plate being adapted for releasable mounting in an optical scanner.

2. The adjustable fixator for scanning dental casts as recited in claim 1, wherein said engaging member comprises a threaded screw.

3. The adjustable fixator for scanning dental casts as recited in claim 2, further comprising a threaded nut for releasable engagement with the threaded screw.

4. The adjustable fixator for scanning dental casts as recited in claim 1, wherein the cylindrical support is mounted on the rear end of the lower plate.

5. The adjustable fixator for scanning dental casts as recited in claim 4, wherein the cylindrical shell is mounted on the rear end of the upper plate.

6. The adjustable fixator for scanning dental casts as recited in claim 1, wherein the top surface of the lower plate includes a magnet.

7. The adjustable fixator for scanning dental casts as recited in claim 6, wherein the bottom surface of the upper plate includes a magnet.

* * * * *